United States Patent
Al-Ali

(10) Patent No.: US 11,291,061 B2
(45) Date of Patent: *Mar. 29, 2022

(54) PATIENT-WORN WIRELESS PHYSIOLOGICAL SENSOR WITH PAIRING FUNCTIONALITY

(71) Applicant: Masimo Corporation, Irvine, CA (US)

(72) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,386

(22) Filed: Jun. 11, 2020

(65) Prior Publication Data

US 2020/0404722 A1    Dec. 24, 2020

Related U.S. Application Data

(63) Continuation of application No. 15/874,652, filed on Jan. 18, 2018, now Pat. No. 10,721,785.

(Continued)

(51) Int. Cl.
*H04W 76/14* (2018.01)
*A61B 5/00* (2006.01)
(Continued)

(52) U.S. Cl.
CPC ........... *H04W 76/14* (2018.02); *A61B 5/0015* (2013.01); *A61B 5/14551* (2013.01); *A61B 5/282* (2021.01); *A61B 5/6833* (2013.01); *H04L 63/18* (2013.01); *H04W 12/50* (2021.01); *A61B 5/01* (2013.01); *A61B 5/021* (2013.01); *A61B 5/053* (2013.01); *A61B 5/113* (2013.01); *A61B 5/369* (2021.01); *A61B 2562/08* (2013.01); *H04W 4/80* (2018.02); *H04W 8/005* (2013.01); *H04W 12/77* (2021.01); *H04W 84/20* (2013.01)

(58) Field of Classification Search
CPC ....... A61B 5/021; A61B 5/0476; A61B 5/053; A61B 5/113; A61B 5/04085; A61B 5/0015; A61B 5/14551; A61B 5/6833; A61B 5/01; A61B 2562/08; H04W 76/14; H04W 12/003; H04W 4/80; H04W 12/00522; H04W 8/005; H04W 84/20; H04L 63/18
USPC ........................................................ 370/329
See application file for complete search history.

(56) References Cited

U.S. PATENT DOCUMENTS 4,960,128 A    10/1990    Gordon et al.
4,964,408 A    10/1990    Hink et al.
(Continued)

FOREIGN PATENT DOCUMENTS

WO    WO-2017087168 A1 *    5/2017    ............. H04L 67/10

*Primary Examiner* — Yemane Mesfin
*Assistant Examiner* — Intekhaab A Siddiquee
(74) *Attorney, Agent, or Firm* — Knobbe, Martens, Olson & Bear, LLP

(57) ABSTRACT

Systems and methods described herein use pairing to associate a wireless sensor with a patient monitoring device such as a bedside patient monitor or a mobile device. A signal emitted by a patient monitoring device can be detected by a wireless sensor. The wireless sensor can be associated with the detected signal and pair the wireless sensor with the patient monitoring device. The wireless sensor can be configured to enter into a patient parameter sensing mode of operation after the association of the wireless sensor with the patient monitoring device.

21 Claims, 12 Drawing Sheets

Related U.S. Application Data

(60) Provisional application No. 62/505,762, filed on May 12, 2017, provisional application No. 62/447,836, filed on Jan. 18, 2017.

(51) Int. Cl.
*A61B 5/1455* (2006.01)
*A61B 5/282* (2021.01)
*H04L 29/06* (2006.01)
*H04W 12/50* (2021.01)
*A61B 5/01* (2006.01)
*A61B 5/021* (2006.01)
*A61B 5/053* (2021.01)
*A61B 5/113* (2006.01)
*A61B 5/369* (2021.01)
*H04W 4/80* (2018.01)
*H04W 8/00* (2009.01)
*H04W 12/77* (2021.01)
*H04W 84/20* (2009.01)

(56) References Cited

U.S. PATENT DOCUMENTS

| | | |
|---|---|---|
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |

(56) References Cited

U.S. PATENT DOCUMENTS

| | | |
|---|---|---|
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |

(56) References Cited

U.S. PATENT DOCUMENTS

| | | |
|---|---|---|
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |

(56) References Cited

U.S. PATENT DOCUMENTS

| | | |
|---|---|---|
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,026,053 B2 * | 5/2015 | Molettiere .......... A61B 5/02055 455/41.2 |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,106,307 B2 | 8/2015 | Molettiere et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |

(56) References Cited

U.S. PATENT DOCUMENTS

| | | |
|---|---|---|
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |

(56) References Cited

U.S. PATENT DOCUMENTS

| | | |
|---|---|---|
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| 11,147,518 B1 | 10/2021 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0113618 A1 | 5/2008 | De Leon et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0072263 A1 | 3/2011 | Bishop et al. |
| 2011/0081860 A1 | 4/2011 | Brown et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |

(56) References Cited

U.S. PATENT DOCUMENTS

| | | |
|---|---|---|
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0065046 A1* | 3/2015 | Wilfred ............... H04L 63/18 455/41.2 |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099943 A1 | 4/2015 | Russell |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0360561 A1 | 12/2016 | Lee et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0010848 A1* | 1/2017 | Hinckley ............... G06F 3/041 |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0214780 A1 | 7/2017 | Gofman et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |

(56) References Cited

U.S. PATENT DOCUMENTS

| | | |
|---|---|---|
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |

* cited by examiner

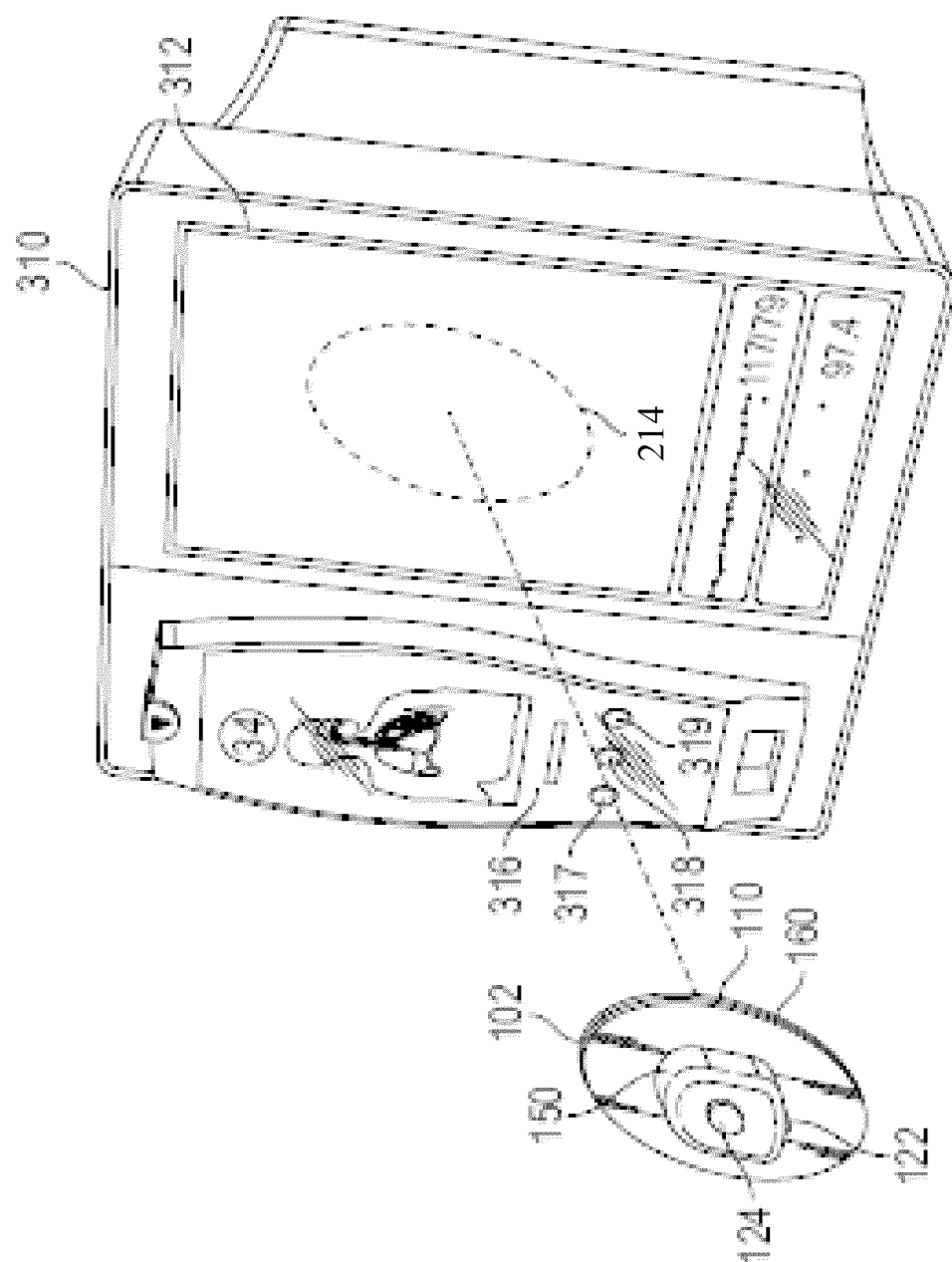

PATIENT-WORN WIRELESS PHYSIOLOGICAL SENSOR WITH PAIRING FUNCTIONALITY

RELATED APPLICATIONS

This application is a continuation of U.S. patent application Ser. No. 15/874,652, filed Jan. 18, 2018, titled "PATIENT-WORN WIRELESS PHYSIOLOGICAL SENSOR WITH PAIRING FUNCTIONALITY", which claims priority benefit under 35 U.S.C. § 119(e) from U.S. Provisional Patent Application Ser. No. 62/505,762, filed May 12, 2017, titled "PATIENT-WORN WIRELESS PHYSIOLOGICAL SENSOR WITH PAIRING FUNCTIONALITY", and also claims priority benefit under 35 U.S.C. § 119(e) from U.S. Provisional Patent Application Ser. No. 62/447,836, filed Jan. 18, 2017, titled "PATIENT-WORN WIRELESS PHYSIOLOGICAL SENSOR WITH PAIRING FUNCTIONALITY", the disclosure of which is hereby incorporated by reference in its entirety.

FIELD OF THE DISCLOSURE

The present disclosure relates to the field of pairing of wireless communication devices. More specifically, the disclosure describes among other things a portable wireless device that communicates with a second device capable of wireless communication with paired electronic devices.

BACKGROUND

In clinical settings, such as hospitals, nursing homes, convalescent homes, skilled nursing facilities, post-surgical recovery centers, and the like, patients are frequently monitored using one more different types of physiological sensors. Various types of sensors include a magnetometer that detects patient movement or orientation to track and prevent patient ulcers, a temperature sensor, an acoustic respiration sensor, an electrocardiogram (ECG) sensor, an electroencephalography (EEG) sensor, one or more pulse oximetry sensors, a moisture sensor, a blood pressure sensor, and an impedance sensor, among other sensors.

Wires leading to and from traditional physiological sensors inhibit patient movement and make it difficult to provide care to a patient. Often sensors are accidentally removed by patient movement. At other times, sensors must be moved or replaced when a patient is moved to a different location or when certain types of care are provided to the patient. Wireless sensors provide a solution to the patient movement and access. However, in busy hospital environments with non-technical staff operating these wireless devices, it can be difficult to correctly configure wireless sensors for communication with the correct monitors.

Similarly, other wireless devices including consumer devices such as, but not limited to, speakers, phones, headphones, watches, keyboards, mice, and so forth, capable of being paired have similar issues. These devices are often used by non-technically oriented users that encounter cumbersome pairing requirements.

SUMMARY

For purposes of summarizing the disclosure, certain aspects, advantages and novel features have been described herein. It is to be understood that not necessarily all such advantages can be achieved in accordance with any particular embodiment disclosed herein. Thus, the embodiments disclosed herein can be embodied or carried out in a manner that achieves or optimizes one advantage or group of advantages as taught or suggested herein without necessarily achieving others.

In certain embodiments, a system for electronically pairing a wireless sensor with a patient monitoring device can include a patient monitoring device, a wireless sensor, and at least one hardware processor. The patient monitoring device can include a first display. The wireless sensor can include a button configured to activate a pairing mode that enables the wireless sensor to electronically pair with the patient monitoring device. The wireless sensor can further comprise an optical detector configured to detect light based signals. The hardware processor can further generate a visual signal from the first display. In some embodiments, the hardware processor can detect the visual signal with the optical detector of the wireless sensor. The hardware processor can associate the wireless sensor with the patient monitoring device based on the detected visual signal, thereby pairing the wireless sensor with the patient monitoring device. The hardware processor can further transmit a confirmation signal from the wireless sensor to indicate that association is complete. The hardware processor can configure the wireless sensor to enter into a patient parameter sensing mode of operation after the association of the wireless sensor with the patient monitoring device.

The system of the preceding paragraph can have any sub-combination of the following features: where the first display is of a first size and the wireless sensor is of a second size, where the second size of the wireless sensor is smaller than the first size of the first display; where the size of the wireless sensor corresponds to a shape of a base of the wireless sensor; where the wireless sensor does not require a separate antenna or any additional components for the pairing with the patient monitoring device; where the wireless sensor does not use a wireless communication protocol for the pairing with the patient monitoring device; where the wireless sensor does not use a wireless communication protocol including a Bluetooth protocol, wifi protocol, or a zigbee protocol; where the one or more hardware processors are configured to detect a shape of the wireless sensor when the wireless sensor is placed directly on the first display and in response to the detected shape, associate the wireless sensor with the patient monitoring device; and where the one or more hardware processors are configured to generate a pattern on the first display and associate the wireless sensor with the patient monitoring device based on a successful placement of the wireless sensor on the first display in relation to the generated pattern.

Additionally, in certain embodiments, a system for electronically pairing a wireless sensor with a patient monitoring device can include a patient monitoring device. The system can include a wireless sensor. The wireless sensor can include a button configured to activate a pairing mode that enables the wireless sensor to electronically pair with the patient monitoring device. The system can include one or more hardware processors. The hardware processor can further generate a signal from the patient monitoring device. The hardware processor can also detect the signal with a detector of the wireless sensor. In some embodiments, the hardware processor can associate the wireless sensor with the patient monitoring device based on the detected signal, thereby pairing the wireless sensor with the patient monitoring device. The hardware processor can also transmit a confirmation signal from the wireless sensor to indicate that association is complete. Moreover, the hardware processor can configure the wireless sensor to enter into a patient parameter sensing mode of operation after the association of the wireless sensor with the patient monitoring device.

The system of the preceding paragraph can have any sub-combination of the following features: where the wireless sensor does not require a separate antenna or any additional components for the pairing with the patient monitoring device; where the wireless sensor does not use a wireless communication protocol for the pairing with the patient monitoring device; where the detector comprises a piezoelectric element; where the signal comprises an acoustic signal and where the wireless sensor is configured to detect the acoustic signal with the piezoelectric element; and where the detector comprises an optical detector and where the signal comprises a visual signal and the wireless sensor is configured to detect the visual signal with the optical detector.

In certain embodiments, a method for electronically pairing a wireless sensor with a patient monitoring device can include generating a signal from the patient monitoring device. The method can also include detecting the signal with a detector of the wireless sensor. In some embodiments, the method can include associating the wireless sensor with the patient monitoring device based on the detected signal, thereby pairing the wireless sensor with the patient monitoring device. Furthermore, the method can include transmitting a confirmation signal from the wireless sensor to indicate that association is complete. The method can also include configuring the wireless sensor to enter into a patient parameter sensing mode of operation after the association of the wireless sensor with the patient monitoring device.

The method of the preceding paragraph can have any sub-combination of the following features: where the wireless sensor does not require a separate antenna or any additional components for the pairing with the patient monitoring device; where the wireless sensor does not use a wireless communication protocol for the pairing with the patient monitoring device; where the detector comprises a piezoelectric element; where the detector comprises an optical detector; further generating a pattern on a first display of the patient monitoring device, where the association is further based on a successful placement of the wireless sensor on the first display in relation to the generated pattern.

BRIEF DESCRIPTION OF THE DRAWINGS

FIGS. 3A-3B are perspective views of a wireless sensor and a patient monitor pairing.

DETAILED DESCRIPTION

Figure 1A:
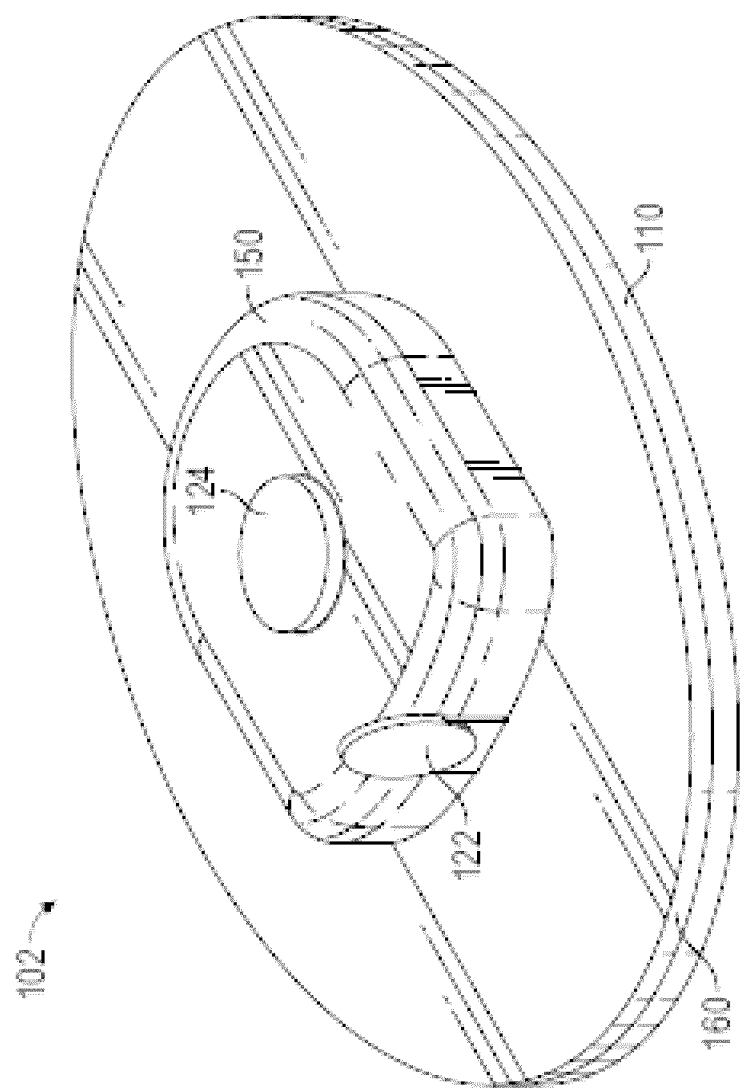
FIG. 1A is a schematic assembled perspective view of a wireless sensor.
Figure 2A:
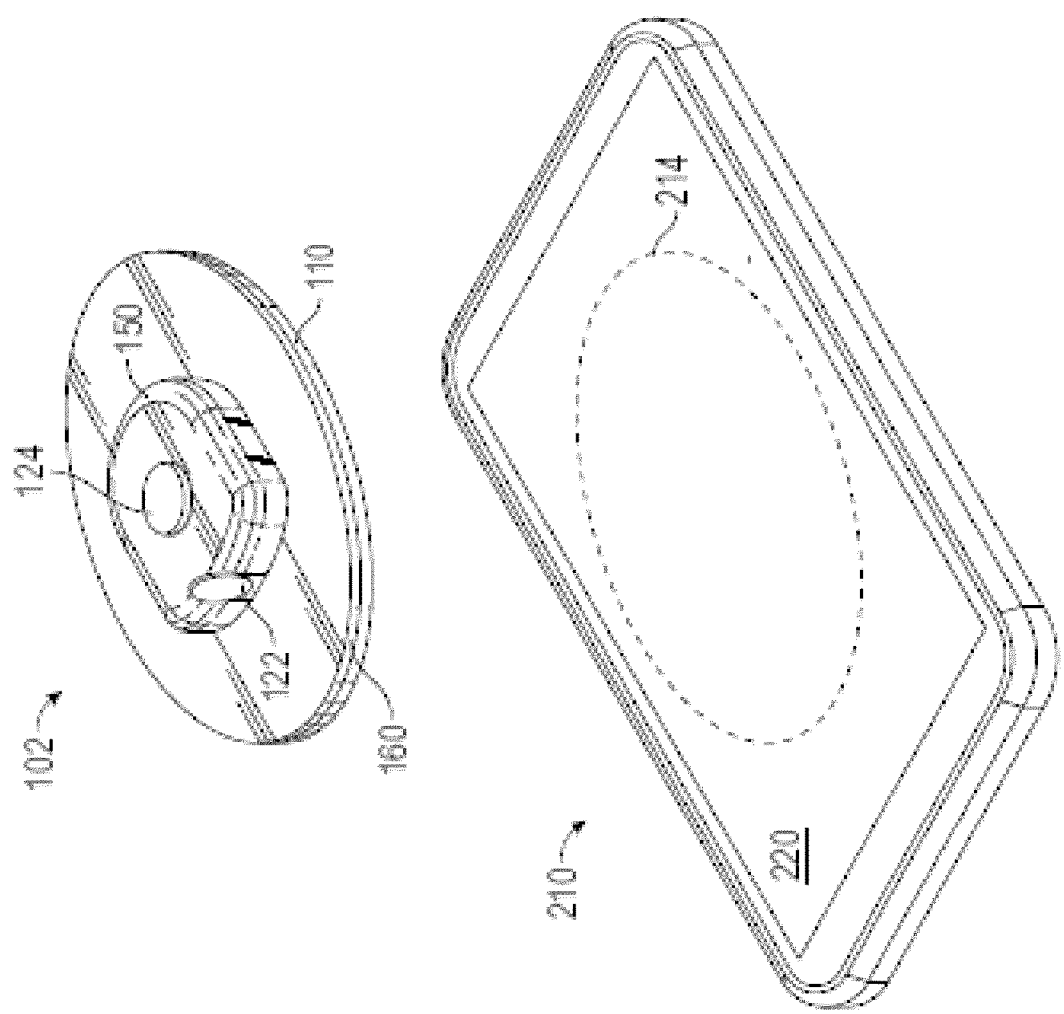
FIG. 2A is a schematic perspective view of a wireless sensor.
Figure 2B:
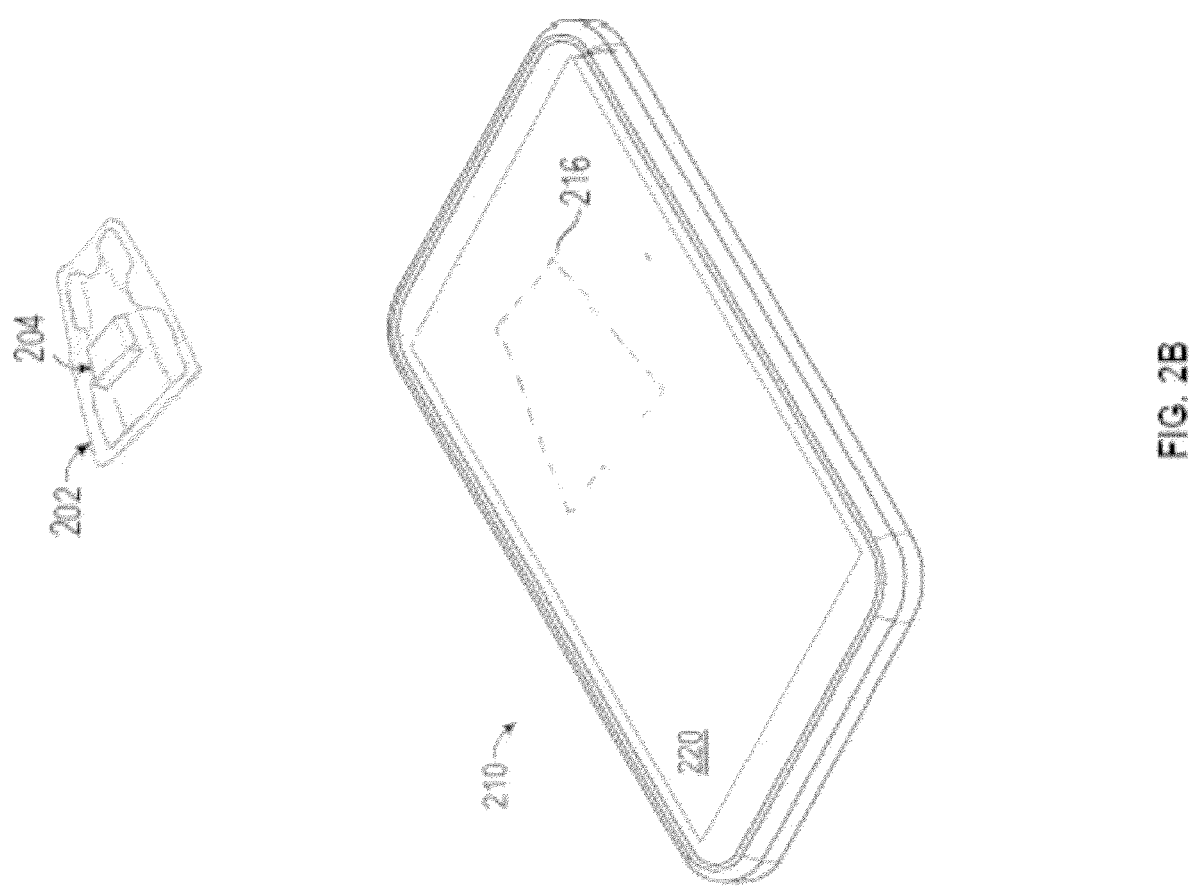
FIG. 2B is a schematic perspective view of a wireless sensor and a mobile device for pairing.
Figure 3B:
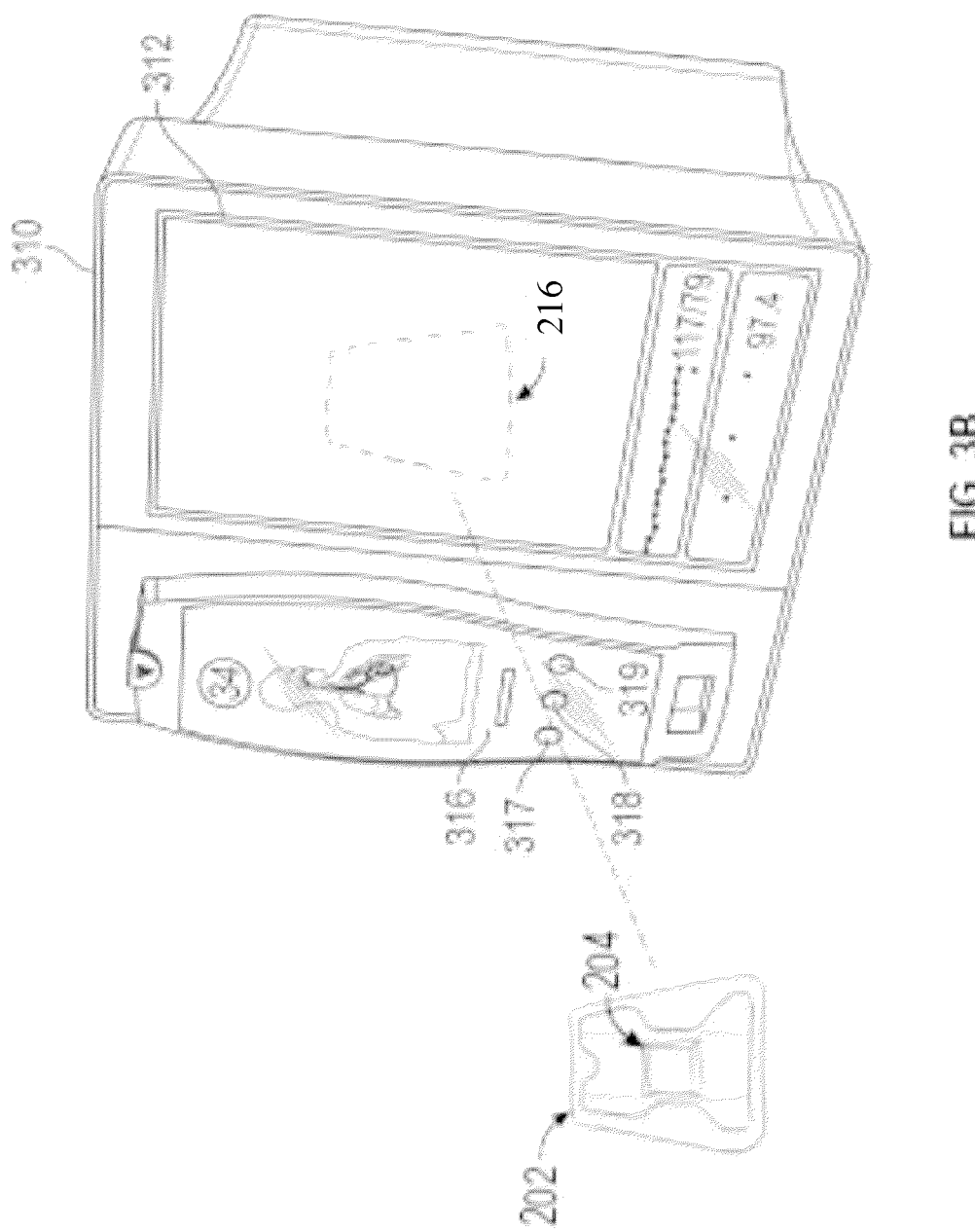

FIG. 1A is a schematic assembled perspective view of wireless sensor 102. The wireless sensor 102 may also be referred to herein as "a wireless physiological sensor 102," "a patient-worn sensor 102," "a movement sensor 102," and "a wearable wireless sensor 102." The wireless sensor 102 includes one or more sensors configured to measure the patient's position, orientation, and motion. Also illustrated in FIG. 1A is a button or switch 124 located on a top portion of the housing 150. The button or switch 124 can be used to change modes of the wireless sensor 102. For example, pressing and holding the button or switch 124 can cause the wireless sensor 102 to switch into a pairing mode of operation. The pairing mode is used to associate the wireless sensor 102 with a mobile device 210 as shown in FIGS. 2A-B or a bedside patient monitor 310 as shown in FIGS. 3A-B. Wireless sensor 102 may include one or more detecting elements such as: a magnetometer which may also be referred to as a compass, a temperature sensor, an acoustic respiration sensor, an electrocardiogram (ECG) sensor, an electroencephalography (EEG) sensor, one or more pulse oximetry sensors, a moisture sensor, a blood pressure sensor, and an impedance sensor.

The magnetometer may be a three-dimensional magnetometer that provides information indicative of magnetic fields, including the Earth's magnetic field. A skilled artisan will understand that the accelerometer, gyroscope, and magnetometer can be integrated into a single hardware component such as an inertial measurement unit. The wireless sensor 102 may be configured to calculate the three-dimensional position and orientation of an object derived from inputs from three sensors attached to the object: an accelerometer configured to measure linear acceleration along three axes; a gyroscope configured to measure angular velocity around three axes; and a magnetometer configured to measure the strength of a magnetic field (such as the Earth's magnetic field) along three axes. The three sensors may attach to the wireless sensor 102 which is affixed to the patient. The sensors may be sampled at a rate between approximately 10 Hz and approximately 100 Hz. One skilled in the art will appreciate that the sensors can be sampled at different rates without deviating from the scope of the present disclosure. The sampled data from the three sensors, which provide nine sensor inputs, are processed to describe the patient's position and orientation in three-dimensional space. The patient's position and orientation are described in terms of Euler angles as a set of rotations around a set of X-Y-Z axes of the patient.

An acoustic respiration sensor can be used to sense acoustic and/or vibrational motion from the patient's body (e.g., the patient's chest) that are indicative of various physiologic parameters and/or conditions, including without limitation, heart rate, respiration rate, snoring, coughing, choking, wheezing, and respiratory obstruction (e.g., apneic events). The ECG sensor can be used to measure the patient's cardiac activity. The ECG sensor may include two electrodes and a single lead. The pulse oximetry sensor(s) can be used to monitor the patient's pulse oximetry, a widely accepted noninvasive procedure for measuring the oxygen saturation level of arterial blood, an indicator of a person's oxygen supply. A typical pulse oximetry system utilizes an optical sensor clipped onto a portion of the patient's body (such as, for example, a fingertip, an ear lobe, a nostril, and the like) to measure the relative volume of oxygenated hemoglobin in pulsatile arterial blood flowing within the portion of the body being sensed. Oxygen saturation (SpO2), pulse rate, a plethysmograph waveform, perfusion index (PI), pleth variability index (PVI), methemoglobin (MetHb), carboxyhemoglobin (CoHb), total hemoglobin (tHb), glucose, and/or otherwise can be measured and monitored using the pulse oximetry sensor(s). The moisture sensor can be used to determine a moisture content of the patient's skin which is a relevant clinical factor in assessing the patient's risk of forming a pressure ulcer. The impedance sensor can be used to track fluid levels of the patient. For example, the impedance sensor can monitor and detect edema, heart failure progression, and sepsis in the patient.

Figure 1B:
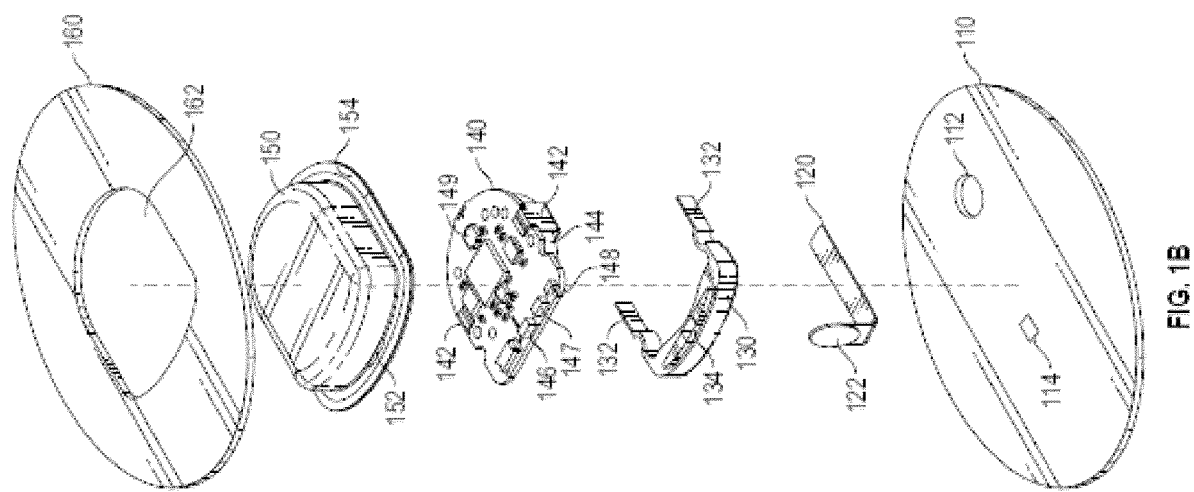
FIG. 1B is a schematic exploded perspective view of a wireless sensor.

FIG. 1B is a schematic exploded perspective view of wireless sensor 102 including a bottom base 110, a removable battery isolator 120, a mounting frame 130, a circuit board 140, a housing 150, and a top base 160. The bottom base 110 is a substrate having a top surface on which various components of the wireless sensor 102 are positioned, and a bottom surface that is used to affix the wireless sensor 102 to the patient's body. The bottom base 110 and top base 160 can be made of medical-grade foam material such as white polyethylene, polyurethane, or reticulated polyurethane foams, to name a few. As illustrated in FIG. 1A, the bottom base 110 and the top base 160 are each in a substantially oval shape, with a thickness of approximately 1 mm. The top base 160 includes a cut-out 162 through which the housing 150 fits during assembly. A skilled artisan will understand that there are numerous sizes and shapes suitable for the top and bottom bases 110 and 160 that can be employed without departing from the scope of the present disclosure. The bottom surface of the bottom base 110 is coated with a high tack, medical-grade adhesive, which when applied to the patient's skin, is suitable for long-term monitoring, such as, for example two days or longer. Portions of the top surface of the bottom base 110 are also coated with a medical-grade adhesive, as the bottom base 110 and the top base 160 are adhered together during assembly of the wireless sensor 102. The bottom base 110 may have apertures 112 and 114. These apertures 112 and 114 may permit transmission of thermal energy, electrical energy, light, sound, or any other input to the wireless sensor 102.

The removable battery isolator 120 is a flexible strip made of an electrically insulating material that serves to block electrical communication between the battery 144 and an electrical contact (not shown) on the circuit board 140. The battery isolator 120 is used to preserve battery power until the wireless sensor 102 is ready for use. The battery isolator 120 blocks electrical connection between the battery 144 and the circuit board 140 until the battery isolator 120 is removed from the wireless sensor 102. The battery isolator 120 can be made of any material that possesses adequate flexibility to be slidably removed from its initial position and adequate dielectric properties so as to electrically isolate the battery 144 from the circuit board 140. For example, the battery isolator 120 can be made of plastic, polymer film, paper, foam, combinations of such materials, or the like. The battery isolator 120 includes a pull tab 122 that extends through a slot 152 of the housing 150 when the wireless sensor 102 is assembled. The pull tab 122 can be textured to provide a frictional surface to aid in gripping and sliding the pull tab 122 out of its original assembled position. Once the battery isolator 120 is removed the battery 144 makes an electrical connection with the electrical contact to energize the electronic components of the wireless sensor 102.

The mounting frame 130 is a structural support element that helps secure the battery 144 to the circuit board 140. The mounting frame 130 has wings 132 that, when assembled are slid between battery holder 142 and the battery 144. Additionally, the mounting frame 130 serves to provide rigid structure between the circuit board 140 and the bottom base 110. The rigid structure, which may include an acoustic respiratory sensor, may transmit vibrational motion (vibrations) emanating from the patient (such as, for example, vibrational motions related to respiration, heartbeat, snoring, coughing, choking, wheezing, respiratory obstruction, and the like) to the accelerometer 149 positioned on the circuit board 140. The mounting frame 130 may have an aperture 134 that extends through the mounting frame 130. The aperture 134 may be aligned with the aperture 114 in the bottom base 110 as described above. The aperture 134 may permit transmission of thermal energy, electrical energy, light, sound, or any other input to the wireless sensor 102. The aperture 134 may be filled with a thermally conductive material.

A battery holder 142 is attached to two sides of the top portion circuit board 140 and extends (forming a support structure) under the bottom side of the circuit board 140 to hold the battery 144 in position relative to the circuit board 140. An electrical connection between the anode of the battery 144 and the circuit board 140 is made by way of the battery holder which is in electrical contact with the anode of the battery 144 and the circuit board 140. The cathode of the battery 144 is positioned to touch a battery contact (not shown) on the bottom side of the circuit board 140.

The housing 150 is a structural component that serves to contain and protect the components of the wireless sensor 102. The housing 150 can be made of any material that is capable of adequately protecting the electronic components of the wireless sensor 102 such as thermoplastics and thermosetting polymers. The housing 150 includes a slot 152 through which the battery isolator 120 is inserted during assembly. The housing 150 also includes a rim 154 that extends around the outer surface of the housing 150. The rim 154 is used to secure the housing 150 in position relative to the bottom base 110 and the top base 160 when the wireless sensor 102 is assembled.

Assembly of the wireless sensor 102 is as follows: the circuit board 140 and battery holder 142 holding the battery 144 are placed into the housing 150. The wings 132 of the mounting frame 130 are inserted in between the battery 144 and the battery holder 142, so as to align the mounting frame 130 with the circuit board 140. The battery isolator 120 is positioned between the electrical contact and the battery 144. The pull tab 122 of the battery isolator 120 is then fed through the slot 152 in the housing 150. The top base 160 is then positioned over the housing 150. The rim 154 of the housing 150 adheres to the bottom surface of the top base 160, which is coated with high tack, medical-grade adhesive. The resulting partial assembly is positioned centrally onto the top surface of the bottom base 110, aligning the edges of the base top 160 with the edges of the base bottom 110. The bottom surface of the bottom base 110 is then coated with a high tack, medical-grade adhesive, and a release liner (not shown) is placed on the bottom surface of the bottom base 110 to protect the adhesive until it is time for use.

FIG. 2A is a perspective illustration of the patient monitoring system in a clinical setting. The patient monitoring system includes a wireless sensor 102 worn by a patient in proximity to mobile device 210. The mobile device 210 includes screen 220 that may be configured to transmit and receive a visual, optical, and/or light-based pairing signal. The pairing signal may contain a pattern containing a shape, color, or a combination of patterns. The pairing signal may involve displaying instructions on a screen 220 for a user to follow. The instructions may include the user placing a wireless sensor 102 of a particular shape and size in a certain position relative to the screen 220. The instructions may be displayed using an object 214 on the screen 220 to represent the silhouette of the wireless sensor 102. To follow the instructions, the user may hold the wireless sensor 102 and position the wireless sensor 102 according to the instructions. The user may place the wireless sensor 102 to resemble the relative position of the object 214 displayed on the screen 220 of the mobile device 210.

The pairing signal may contain a series of visual, optical, and/or light based signals. The series of signals may utilize variations in color, shade, shape, or visual patterns. The pairing signal may contain a series of flashes, wherein the flashes may vary in intensity or duration. The pairing signal may comprise a combination of visual and audio signals.

For example, the wireless sensor 102 and the mobile device 210 may include a detector that detects visual, optical, or light-based signals and another detector for detecting audio sound or a series of audio sounds. A detector may be configured to detect both visual and audio signals. The pairing signal may include a sequence of visual signals that is synchronized with a sequence of audio signals.

Additionally, the screen 220 may be configured to display motion instructions for a care provider to perform in order to generate motion signals representing a pairing signal. Mobile device 210 may also generate audio-based pairing signals using a speaker (not shown). The sounds may be tuned to a frequency within or outside of the range of human hearing and may comprise various rings or tones. Additionally, the mobile device 210 may have a port for connecting peripheral devices that may generate various signals such as current or voltage based signals. The pairing signal may take the form of an electrical signal.

FIG. 2B is a perspective illustration of the patient monitoring system in a clinical setting. The patient monitoring system includes a wireless sensor 202 worn by a patient in proximity to mobile device 210. The mobile device 210 includes screen 220 that may be configured to transmit a visual, optical, and/or light-based pairing signal. The pairing signal may contain a pattern containing a shape, color, or a combination of patterns. The pairing signal may involve displaying instructions on a screen 220 for a user to follow. The instructions may include the user placing a wireless sensor 202 of a particular shape and size in a certain position relative to the screen 220. The shape and size of the wireless sensor 202 may differ from the shape and size of the wireless sensor 102. The instructions may be displayed using an object 216 on the screen 220 to represent the silhouette of the wireless sensor 202. To follow the instructions, the user may hold the wireless sensor 202 and position the wireless sensor 202 according to the instructions. The user may place the wireless sensor 202 to resemble the relative position of the object 216 displayed on the screen 220 of the mobile device 210.

The pairing signal may contain a series of visual, optical, and/or light based signals. The series of signals may utilize variations in color, shade, shape, or visual patterns. The pairing signal may contain a series of flashes, wherein the flashes may vary in intensity or duration. Mobile device 210 may also generate audio-based pairing signals using a speaker (not shown). The sounds may be tuned to a frequency within or outside of the range of human hearing and may comprise various rings or tones. The pairing signal may comprise a combination of visual and audio signals. For example, the wireless sensor 102 and the mobile device 210 may include a detector that detects visual, optical, or light-based signals and another detector for detecting audio sound or a series of audio sounds. A detector may be configured to detect both visual and audio signals. The pairing signal may include a sequence of visual signals that is synchronized with a sequence of audio signals.

Additionally, the screen 220 may be configured to display motion instructions for a care provider to perform in order to generate motion signals representing a pairing signal. Additionally, the mobile device 210 may have a port for connecting peripheral devices that may generate various signals such as current or voltage based signals. The pair signal may take the form of an electrical signal.

Wireless sensor 202 may include a probe for taking non-invasive optical measurements. The probe may have an emitter for transmitting an optical signal and a detector for detecting the optical signal transmitted by the emitter. The probe may have a flexible circuit assembly with circuit paths to connect the emitter and the detector. The detector may be further configured to detect the pairing signal emitted by mobile device 210.

The wireless sensor 202 may also include a button or switch 204. The button or switch 204 can be used to change modes of the wireless sensor 202. For example, pressing and holding the button or switch 204 can cause the wireless sensor 202 to switch into a pairing mode of operation. The pairing mode is used to associate the wireless sensor 102 with a mobile device 210 or a bedside patient monitor 310.

FIG. 3A is a perspective illustration of the patient monitoring system in a clinical setting. The patient monitoring system includes a wireless sensor 102 worn by a patient in proximity to a bedside patient monitor 310 located at the side of a patient's bed. The bedside patient monitor 310 may include screen 312 that may be configured to transmit a visual, optical, and/or light-based pairing signal. The pairing signal may contain a pattern containing a shape, color, or a combination of patterns. The pairing signal may involve displaying instructions on a screen 312 for a user to follow.

The instructions may include the user placing a wireless sensor 102 of a particular shape and size in a certain position relative to the screen 312. The instructions may be displayed using an object 214 on the screen 312 to represent the silhouette of the wireless sensor 102. To follow the instructions, the user may hold the wireless sensor 102 and position the wireless sensor 102 according to the instructions. The user may place the wireless sensor 102 to resemble the relative position of the object 214 displayed on the screen 312 of the bedside patient monitor 310.

The pairing signal may contain a series of visual, optical, and/or light based signals. The series of signals may utilize variations in color, shade, shape, or visual patterns. Additionally, the pairing signal may contain a series of flashes, wherein the flashes may vary in intensity or duration. Additionally, the screen 312 may be configured to display motion instructions for a care provider to perform in order to generate motion signals representing a pairing signal. Bedside patient monitor 310 may also generate audio-based pairing signals using a speaker (not shown). The sounds may be tuned to a frequency within or outside of the range of human hearing and may comprise various rings or tones. Additionally, the bedside patient monitor 310 may have a port 316 for connecting peripheral devices that may generate various signals such as current or voltage based signals. The pairing signal may take the form of an electrical signal.

The patient monitor 310 may have a button or switch 317 can be used to activate the patient monitor 310 and place it in the pairing mode of operation. Similarly the buttons or switches 318, 319 can also be used to activate the patient monitor 310 and place it in the pairing mode of operation. This process is discussed more below. When the button/switch 317 is depressed and/or continuously held down, the patient monitor 310 may enter into the pairing mode of operation.

FIG. 3B is a perspective illustration of the patient monitoring system in a clinical setting. The patient monitoring system includes a wireless sensor 202 worn by a patient in proximity to a bedside patient monitor 310 located at the side of a patient's bed. The bedside patient monitor 310 may include screen 312 that may be configured to transmit a visual, optical, and/or light-based pairing signal. The pairing signal may contain a pattern containing a shape, color, or a combination of patterns. The pairing signal may involve displaying instructions on a screen 312 for a user to follow.

Similar to FIG. 3A, the instructions may include the user placing a wireless sensor 202 of a particular shape and size in a certain position relative to the screen 312. The instructions may be displayed using an object 216 on the screen 312 to represent the silhouette of the wireless sensor 202. To follow the instructions, the user may hold the wireless sensor 202 and position the wireless sensor 202 according to the instructions. The user may place the wireless sensor 202 to resemble the relative position of the object 216 displayed on the screen 312 of the bedside patient monitor 310.

Although described with respect to a bedside patient monitor 310, it is to be understood that mobile device 210 may also perform some or all of the functionality described in relation to bedside patient monitor 310. For example, wireless sensor 102 may pair with either the mobile device 210 or bedside patient monitor 310. Additionally, one skilled in the art will appreciate that numerous types of patient-specific information may be collected and analyzed by either the mobile device 210 or bedside patient monitor 310. Therefore, it is to be understood that patient monitoring system may be implemented with a mobile device 210 or a bedside patient monitor 310.

In some scenarios, it may be desirable to pair, or associate, the wireless sensor 102 with the bedside patient monitor 310 or mobile device 210 to avoid interference from other wireless devices and/or to associate patient-specific information (stored, for example, on the patient monitor 310) with the sensor data that is being collected and transmitted by the wireless sensor 102. Illustratively, such patient-specific information can include, by way of non-limiting example, the patient's name, age, gender, weight, identification number (e.g., social security number, insurance number, hospital identification number, or the like), admission date, length of stay, physician's name and contact information, diagnoses, type of treatment, perfusion rate, hydration, nutrition, pressure ulcer formation risk assessments, patient turn protocol instructions, treatment plans, lab results, health score assessments, and the like. One skilled in the art will appreciate that numerous types of patient-specific information can be associated with the described patient-worn sensor without departing from the scope of the present disclosure. Additionally, pairing the wireless sensor 102 with the mobile device 210 or bedside patient monitor 310 can be performed to provide data security and to protect patient confidentiality. Some wireless systems require the care provider to program the wireless sensor 102 to communicate with the correct mobile device 210 or bedside patient monitor 310. Other wireless systems require a separate token or encryption key and several steps to pair the wireless device 102 with the correct bedside patient monitors 310. Some systems require the token to be connected to the mobile device 210 or the bedside patient monitor 310, then connected to the wireless device 102, and then reconnected to the mobile device 210 or bedside patient monitor 310. In certain scenarios, it may be desirable to share wireless communication information between a wireless sensor 102 and a mobile device 210 or bedside patient monitor 310 without a separate token or encryption key. For security purposes, it may be desirable to use security tokens to ensure that the correct patient monitor 310 receives the correct wirelessly transmitted data. Security tokens prevent the mobile device 210 or bedside patient monitor 310 from accessing the transmitted data unless the wireless sensor 102 and mobile device 210 or patient monitor 310 share the same password. The password may be a word, passphrase, or an array of randomly chosen bytes.

Figure 4:
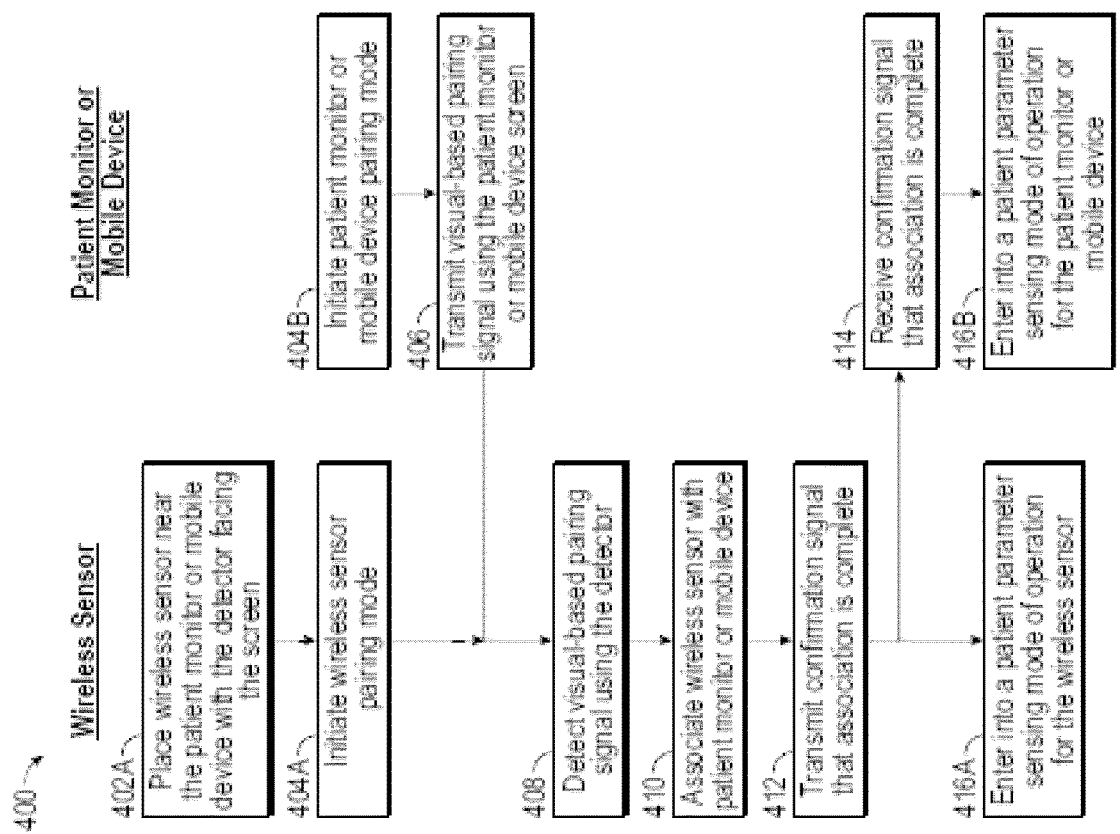
FIG. 4 is a flow diagram describing a process to pair a wireless sensor with a patient monitor.

FIG. 4 illustrates a method of associating a wireless sensor 102 with a mobile device 210 or a bedside patient monitor 310, which may be referred to as "pairing." At block 402A, the wireless sensor 102 may be placed near the mobile device 210 or the bedside patient monitor 310 in preparation for receiving a pairing signal. A visual, optical, and/or light-based detector 146 of the wireless sensor 102 may be physically oriented and configured to receive a pairing signal in the form of a visual, optical, and/or light-based pairing signal. The pairing signal may contain a pattern containing a shape, color, or a combination of patterns. The pairing signal may contain a series of visual, optical, and/or light based signals. The series of signals may utilize variations in color, shade, shape, or visual patterns. Additionally, the pairing signal may contain a series of flashes, wherein the flashes may vary in intensity or duration. The signal may be unique to the wireless sensor 102 and the mobile device 210 or the bedside patient monitor 310. By using a pairing signal that uniquely identifies the wireless sensor 102 and the mobile device 210 or the bedside patient monitor 310, a secure connection may be established between the two paired devices.

Various types of sensors can be used with the pairing process of the present disclosure. For example, a pulse oximeter sensor can be paired by facing its light detector toward a bedside patient monitor screen 312 or mobile device screen 220 to receive a visual, optical, and/or light based signal. In another example, an ulcer sensor can be paired by receiving a pairing signal in the form of detected motion. Similarly, other types of wireless sensors can be paired using the included detectors. For example, an acoustic sensor can be paired based on audio signals emitted from the patient monitor 310. EEG and ECG wireless sensors can be paired using small electrical impulses from a special conductor included as part of the patient monitor 310. Other sensors can be paired in a similar fashion depending on the specific detectors included on the wireless sensors.

Returning to block 402A, the wireless sensor 102 may be placed in proximity to the mobile device 210 or the bedside patient monitor 310 such that the visual, optical, and/or light-based detector 146 may receive the visual, optical, and/or light-based pairing signal. The visual, optical, and/or light-based pairing signal may have a pairing signal transmission range of up to approximately three inches. The visual, optical, and/or light-based pairing signal may have a pairing signal transmission range of up to approximately six inches. The visual, optical, and/or light-based pairing signal may have a pairing signal transmission range of up to approximately one foot (i.e., twelve inches) or farther. A skilled artisan will recognize that other ranges can be used for the pairing signal transmission range.

At block 404A the wireless sensor 102 is set to operate in a pairing mode. A user may begin by initiating the pairing mode of operation for the wireless sensor 102. This may include powering on the wireless sensor 102, switching the wireless sensor 102 to a special pairing state, and/or the like. For example, the wireless sensor 102 may include a battery isolator 120 which, when removed, activates the wireless sensor 102. Upon activation, the default mode of operation is the pairing mode. The wireless sensor 102 may have a button or switch 124 that can be used to activate the wireless sensor 102 and place it in the pairing mode of operation. For example, a depressible button or switch 124 can be located on the top portion of the housing 150. When the button or switch 124 is depressed and continuously held down, the wireless sensor 102 enters into the pairing mode of operation and remains in the pairing mode of operation for as long as the button or switch 124 is depressed. The wireless sensor 102 enters into the pairing mode by activating the visual, optical, and/or light-based sensor 146. Once activated, the optical sensor 146 may be configured to receive the visual, optical, and/or light-based pairing signal. Similarly, the wireless sensor 202 may have a button or switch 204 that can be used to activate the wireless sensor 202 and place it in the pairing mode of operation.

At block 404B, the mobile device 210 or bedside patient monitor 310 is set to operate in pairing mode. A user may begin by initiating the pairing mode of operation for the mobile device 210 or the bedside patient monitor 310. This may include powering on the mobile device 210 or the bedside patient monitor 310, switching the mobile device 210 or the bedside patient monitor 310 to a special pairing state, and/or the like. The bedside patient monitor 310 may have a button or switch 317 that can be used to activate the patient monitor 310 and place it in the pairing mode of operation. When the button or switch 317 is depressed and/or continuously held down, the patient monitor 310 enters into the pairing mode of operation. Similarly, the mobile device 210 may have a button or switch that can be used to activate the mobile device 210 and place it in the pairing mode of operation. When the button or switch is depressed and/or continuously held down, the mobile device 210 enters into the pairing mode of operation.

As reflected at block 406, the mobile device 210 or the bedside patient monitor 310 transmits a pairing signal to pair, or associate, with wireless sensor 102. The patient monitor screen 312 or mobile device screen 220 may be configured to emit a pairing signal. The mobile device screen 220 or patient monitor screen 312 may be configured to emit a visual, optical, and/or light-based pairing signal. The pairing signal transmission is received by orienting the visual, optical, and/or light-based detector 146 of the wireless sensor 102 toward the mobile device screen 220 or the patient monitor screen 312. The limited range of the visual, optical, and/or light-based pairing signal helps to prevent unintended or incidental association of the wireless sensor 102 with a mobile device 210 or bedside patient monitor 310 that might be nearby but which is not intended to be paired with the wireless sensor 102. Such circumstances can occur in hospitals, healthcare facilities, nursing homes, and the like where wireless sensors 102 mobile devices 210, and bedside patient monitors 310 are located in close physical proximity to one another.

At block 408, the wireless sensor 102 detects the pairing signal from bedside patient monitor 310 or mobile device 210. Upon detection of the pairing signal, at block 410, the wireless sensor 102 associates with the bedside patient monitor 310 thereby configuring the wireless sensor 102 and mobile device 210 or the patient monitor 310 to communicate with each other. Once the pairing is completed, the wireless sensor 102 transmits a confirmation signal confirming that the patient-worn sensor 102 is associated with the mobile device 210 or the bedside patient monitor 310, thereby indicating that the pairing process has been successfully completed, as reflected in block 412. At block 414, the mobile device 210 or the bedside patient monitor 310 receives the confirmation signal. And at block 416A, the wireless sensor 102 exits the pairing mode of operation and enters into a patient parameter sensing mode of operation. Similarly, at block 416B, the mobile device 210 or the bedside patient monitor 310 enters a patient parameter sensing mode of operation.

Figure 5:
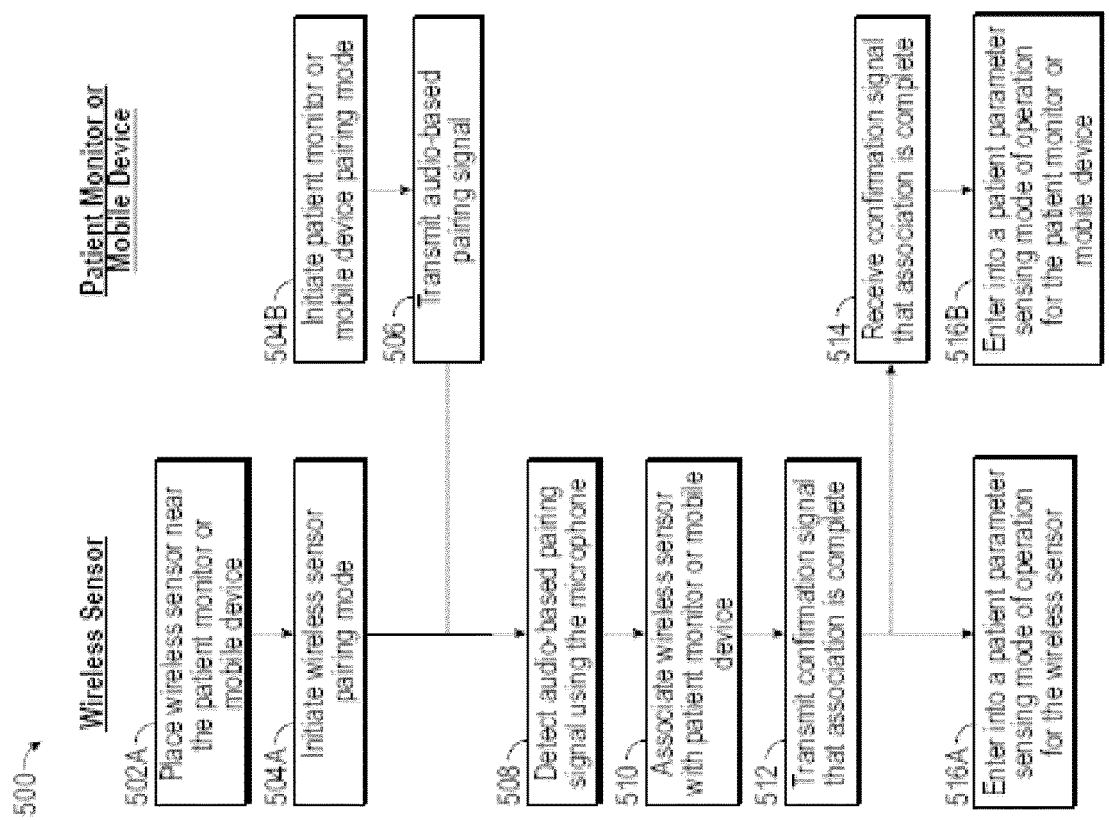
FIG. 5 is a flow diagram describing a process to pair a wireless sensor with a patient monitor.

FIG. 5 illustrates a method of associating a wireless sensor 102 with a mobile device 210 or the bedside patient monitor 310, which may be referred to as "pairing." At block 502A, the wireless sensor 102 may be placed near the mobile device 210 or the bedside patient monitor 310 in preparation for receiving a pairing signal. For sensors that utilize an audio sensor, such as respirator sensor, the pairing signal may be an audio sound or a series of audio sounds. A sound or audio-based detector 147 of the wireless sensor 102 may be configured to receive a pairing signal in the form of a sound or audio-based pairing signal. The sounds may be tuned to a frequency within or outside of the range of human hearing and may comprise various rings, chimes, or tones. The series of audio sounds may utilize variations in volume or tone to transmit pairing information. The signal may be unique to the wireless sensor 102 and the mobile device 210 or the patient monitor 310. By using a pairing signal that uniquely identifies the wireless sensor 102 and the mobile device 210 or the patient monitor 310, a secure connection may be established between the two paired devices.

Various types of sensors can be used with the pairing process of the present disclosure. For example, a pulse oximeter sensor can be paired by facing its light detector toward a patient monitor display 312 or mobile device display 220 to receive a visual, optical, and/or light based signal. In another example, an ulcer sensor can be paired by receiving a pairing signal in the form of detected motion. Similarly, other types of wireless sensors can be paired using the included detectors. For example, an acoustic sensor can be paired based on audio signals emitted from the mobile device 210 or the bedside patient monitor 310. EEG and ECG wireless sensors can be paired using small electrical impulses from a special conductor included as part of the patient monitor 310. Other sensors can be paired in a similar fashion depending on the specific detectors included on the wireless sensors.

Returning to block 502A, the wireless sensor 102 may be placed in proximity to the mobile device 210 or the bedside patient monitor 310 such that the sound or audio detector 147 may receive the sound or audio-based pairing signal. The sound or audio-based pairing signal has a pairing signal transmission range of up to approximately three inches. The sound or audio-based pairing signal may have a pairing signal transmission range of up to approximately six inches. The sound or audio-based pairing signal may have a pairing signal transmission range of up to approximately one foot (i.e., twelve inches) or farther. A skilled artisan will recognize that other ranges can be used for the pairing signal transmission range.

At block 504A the wireless sensor 102 is set to operate in a pairing mode. A user may begin by initiating the pairing mode of operation for the wireless sensor 102. This may include powering on the wireless sensor 102, switching the wireless sensor 102 to a special pairing state, and/or the like. For example, the wireless sensor 102 may include a battery isolator 120 which, when removed, activates the wireless sensor 102. Upon activation, the default mode of operation is the pairing mode. The wireless sensor 102 may have a button or switch 124 that can be used to activate the wireless sensor 102 and place it in the pairing mode of operation. For example, a depressible button or switch 124 can be located on the top portion of the housing 150. When the button or switch 124 is depressed and continuously held down, the wireless sensor 102 enters into the pairing mode of operation and remains in the pairing mode of operation for as long as the button or switch 124 is depressed. The wireless sensor 102 enters into the pairing mode by activating the sound or audio-based sensor 147. Once activated, the sound or audio-based sensor 147 may be configured to receive the audio or sound-based pairing signal.

At block 504B, the mobile device 210 or the bedside patient monitor 310 is set to operate in pairing mode. A user may begin by initiating the pairing mode of operation for the mobile device 210 or the bedside patient monitor 310. This may include powering on the device, switching the device to a special pairing state, and/or the like. The bedside patient monitor 310 may have a button or switch 317 that can be used to activate the bedside patient monitor 310 and place it in the pairing mode of operation. When the button or switch 317 is depressed and/or continuously held down, the patient monitor 310 enters into the pairing mode of operation.

As reflected at block 506, the mobile device 210 or the bedside patient monitor 310 transmits a pairing signal to pair, or associate, with wireless sensor 102. The mobile device 210 or the bedside patient monitor 310 is configured to emit a pairing signal. The speaker of the mobile device 210 or the bedside patient monitor 310 may be configured to emit an audio signal or a series of audio sounds as the pairing signal. The pairing signal transmission is received by orienting the audio or sound-based detector 147 of the wireless sensor 102 toward the bedside patient monitor 310 or mobile device 210. The limited range of the audio or sound-based pairing signal helps to prevent unintended or incidental association of the wireless sensor 102 with a mobile device or bedside patient monitor 310 that might be nearby but which is not intended to be paired with the wireless sensor 102. Such circumstances can occur in hospitals, healthcare facilities, nursing homes, and the like where wireless sensors 102 and the mobile device 210 or the bedside patient monitor 310 are located in close physical proximity to one another.

At block 508, the wireless sensor 102 detects the pairing signal from the mobile device 210 or the patient monitor 310. Upon detection of the pairing signal, the wireless sensor 102, at block 510, associates with the mobile device 210 or the bedside patient monitor 310 thereby configuring the wireless sensor 102 and patient monitor 310 to communicate with each other. Once the pairing is completed, the wireless sensor 102 transmits a confirmation signal confirming that the patient-worn sensor 102 is associated with the mobile device 210 or the bedside patient monitor 310, thereby indicating that the pairing process has been successfully completed, as reflected in block 512. At block 514, the mobile device 210 or the bedside patient monitor 310 receives the confirmation signal. And at block 516A, the wireless sensor 102 exits the pairing mode of operation and enters into a patient parameter sensing mode of operation. Similarly, at block 516B, the mobile device 210 or the bedside patient monitor 310 enters a patient parameter sensing mode of operation. In the patient parameter sensing mode of operation, the patient-worn sensor 102 transmits a patient parameter sensing signal having a patient parameter sensing signal transmission range. The wireless sensor 102 increases the power of the patient parameter sensing signal transmission range to a standard operating range, such as for example, approximately three meters. The patient parameter sensing signal transmission range may be approximately ten feet. Alternatively, the patient parameter sensing signal transmission range may be approximately thirty feet. The pairing signal transmission range may be between approximately three and twelve inches, while the patient parameter sensing signal transmission range may be approximately ten feet. There may be at least an order of magnitude difference between the pairing signal transmission range and the patient parameter sensing signal transmission range. Thus, the pairing signal transmission range is substantially less than the patient parameter sensing transmission range. Once the wireless sensor 102 enters into the patient parameter sensing mode of operation, the wireless sensor 102 is then in condition to be placed on the patient to perform sensing and monitoring functions.

The patient monitor 310 may access the patient's health records and clinician input via a data network. Illustratively, the patients' positional history data, analyzed in view of the patient's health records, may reveal or suggest a treatment protocol) that will likely yield favorable clinical outcomes for the particular patient. Accordingly, the mobile device 210 or the bedside patient monitor 310 analyzes the accessed information in conjunction with the received information from the wireless sensor 102 to determine a recommended treatment protocol for the patient.

In another aspect of the present disclosure, the mobile device 210 or the bedside patient monitor 310 can determine a score that describes the patient's wellness/sickness state, which may also be referred to as a "Halo Index." Illustratively, the patient monitor 310 accesses and analyzes the patient's health records, clinician input, positional history data provided by the wireless sensor, surface structure pressure data, and other physiological parameter data collected and provided by the wireless sensor (such as, by way of non-limiting example, the patient's temperature, respiration rate, heart rate, ECG signal, and the like) to assess the patient's overall health condition.

An extender/repeater may be used to communicate with the wireless sensor 102 instead of the mobile device 210 or the bedside patient monitor 310. Pairing with the extender/repeater may be performed in the same manner described above with respect to FIG. 4 or FIG. 5.

In another aspect of the present disclosure, the pairing procedures may be applicable to user products including phones, tablets, headphones, watches, speakers, computer mice, computer keyboards, wearable devices, audio headsets, virtual reality headsets, augmented reality headsets, vehicle consoles, infotainment systems, and any other wireless communication devices known to those of skill in the art.

The wireless communication device may be a mobile phone. The mobile phone may allow voice calls to establish a data connection using a cellular network or Wi-Fi network. The mobile phone may also include features in the operating system or mobile applications that offer various functionalities for the user. The wireless communication device may be configured to collect various data such as the GPS location of the mobile phone. The mobile applications may be configured to receive collected data from wireless devices that are paired with the mobile phone.

The wireless communication device may be a wireless headphone that emits audio signals from an audio source. The audio signal may be transmitted through a wireless data connection established using the disclosed pairing procedures. The wireless communication device may be a watch, headset, or other wear device. The device may provide functionality such as detecting the location, movement, physical activity, or physiological condition of the user. The detected data may be transmitted to another wireless device for display, storage, analysis, or other uses. The transmission of the detected data may be facilitated by a wireless data connection established using the disclosed pairing procedures. A wireless data connection may be established to facilitate the use of wireless communication device such as a wireless keyboard or wireless computer mouse. The wireless communication device may be connected to another wireless communication device such as a desktop computer or mobile device such as a laptop or tablet. The transmission of data associated with the functionality of the wireless communication device may be facilitated by a wireless data connection established using the disclosed pairing procedures.

The wireless communication device may be a vehicle console or infotainment system. The vehicle console or infotainment system may include a screen for displaying the operation of the vehicle. The screen may be a touch screen that functions as a control interface for the vehicle. The console or infotainment system may receive data such as an audio signal, video signal, GPS location, driving directions, or fare calculations from a paired wireless communication device. A skilled artisan would recognize that other data may be exchanged between the vehicle console or infotainment system and a paired wireless communication device. The transmission of data associated with the functionality of the wireless communication device and vehicle console or infotainment system may be facilitated by a wireless data connection established using the disclosed pairing procedures.

Figure 6:
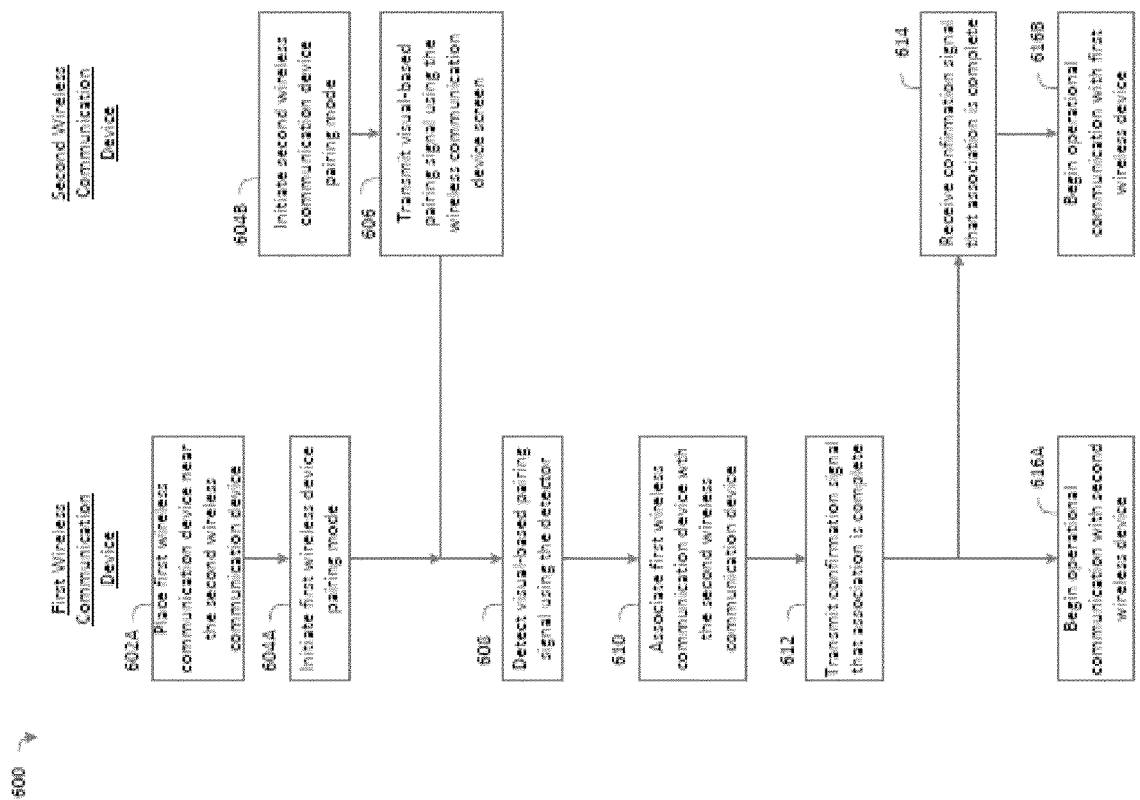
FIG. 6 is a flow diagram describing a process to pair a first wireless device with a second wireless device.

FIG. 6 illustrates a method of associating a first wireless device with a second wireless device, which may be referred to as "pairing." The first wireless device may be a wireless sensor 102 or 202 as described above. The second wireless device may be a mobile device 210 or bedside patient monitor 310 as described above. At block 602A, the first wireless device may be placed near the second wireless device in preparation for receiving a pairing signal. A visual, optical, and/or light-based detector 146 of the first wireless communication device may be physically oriented and configured to receive a pairing signal in the form of a visual, optical, and/or light-based pairing signal. The pairing signal may contain a pattern containing a shape, color, or a combination of patterns. The pairing signal may contain a series of visual, optical, and/or light based signals. The series of signals may utilize variations in color, shade, shape, or visual patterns. The pairing signal may contain a series of flashes, wherein the flashes may vary in intensity or duration. The signal may be unique to the first wireless device and/or the second wireless device. By using a pairing signal that uniquely identifies the first wireless device and/or the second wireless device, a secure connection may be established between the two paired devices.

Various types of sensors can be used with the pairing process of the present disclosure. For example, a pulse oximeter sensor can be paired by facing its light detector toward the display or screen of second wireless communication device to receive a visual, optical, and/or light based signal. In another example, an ulcer sensor can be paired by receiving a pairing signal in the form of detected motion. Similarly, other types of wireless sensors can be paired using the already included detectors that are used for physiological detection or other detection of the surrounding environment during normal use. For example, an acoustic sensor can be paired based on audio signals emitted from the second wireless communications device. EEG and ECG wireless sensors can be paired using small electrical impulses from a special conductor included as part of the second wireless communications device. Other sensors can be paired in a similar fashion depending on the specific detectors included on the first wireless communication device.

Returning to block 602A, the first wireless device may be placed in proximity to the second wireless device such that the visual, optical, and/or light-based detector 146 may receive the visual, optical, and/or light-based pairing signal. The visual, optical, and/or light-based pairing signal has a pairing signal transmission range of up to approximately three inches. The visual, optical, and/or light-based pairing signal has a pairing signal transmission range of up to approximately six inches. The visual, optical, and/or light-based pairing signal has a pairing signal transmission range of up to approximately one foot (i.e., twelve inches) or farther. A skilled artisan will recognize that other ranges can be used for the pairing signal transmission range.

At block 604A the first wireless device is set to operate in a pairing mode. A user may begin by initiating the pairing mode of operation for the first wireless device. This may include powering on the first wireless device, switching the first wireless device to a special pairing state, and/or the like. For example, the first wireless device may include a battery isolator 120 which, when removed, activates the first wireless device. Upon activation, the default mode of operation is the pairing mode. The first wireless device may have a button/switch 124 that can be used to activate the first wireless device and place it in the pairing mode of operation. For example, a depressible button/switch 124 can be located on the top portion of the housing 150. When the button/switch 124 is depressed and continuously held down, the first wireless device enters into the pairing mode of operation and remains in the pairing mode of operation for as long as the button/switch 124 is depressed. The first wireless device may enter into the pairing mode by activating the sound or audio-based sensor 147. Once activated, the sound or audio-based sensor 147 may be configured to receive the audio or sound-based pairing signal.

At block 604B, the second wireless device is set to operate in pairing mode. A user may begin by initiating the pairing mode of operation for the second wireless device. This may include powering on the device, switching the device to a special pairing state, and/or the like. The second wireless device may have a button or switch that can be used to activate the second wireless device and place it in the pairing mode of operation. When the button or switch is depressed or continuously held down, the second wireless device enters into the pairing mode of operation.

As reflected at block 606, the second wireless device transmits a pairing signal to pair, or associate, with first wireless device. The second wireless communications device may be configured to emit a pairing signal. The display or screen of the second wireless communication device may be configured to emit a visual, optical, and/or light-based pairing signal. The pairing signal transmission is received by orienting the visual, optical, and/or light-based detector 146 of the first wireless communication device toward the display or screen. The limited range of the visual, optical, and/or light-based pairing signal helps to prevent unintended or incidental association of the first wireless communication device with a second wireless communication device that might be nearby but which is not intended to be paired with the first wireless communication device. Such circumstances can occur in residential buildings, office buildings, commercial facilities, airports, public transportation facilities, hospitals, healthcare facilities, nursing homes, and the like where the first wireless communications device and second communications device are located in close physical proximity to one another.

At block 608, the first wireless device detects the pairing signal from second wireless device. Upon detection of the pairing signal, the first wireless device, at block 610, associates with the second wireless device thereby configuring the first wireless device and second wireless device to communicate with each other. Once the pairing is completed, the first wireless device transmits a confirmation signal confirming that the first wireless communication device is associated with the second wireless device, thereby indicating that the pairing process has been successfully completed, as reflected in block 612. At block 614, the second wireless device receives the confirmation signal. And at block 616A, the first wireless device exits the pairing mode of operation and enters into a patient parameter sensing mode of operation. Similarly, at block 616B, the second wireless device enters a patient parameter sensing mode of operation.

Figure 7:
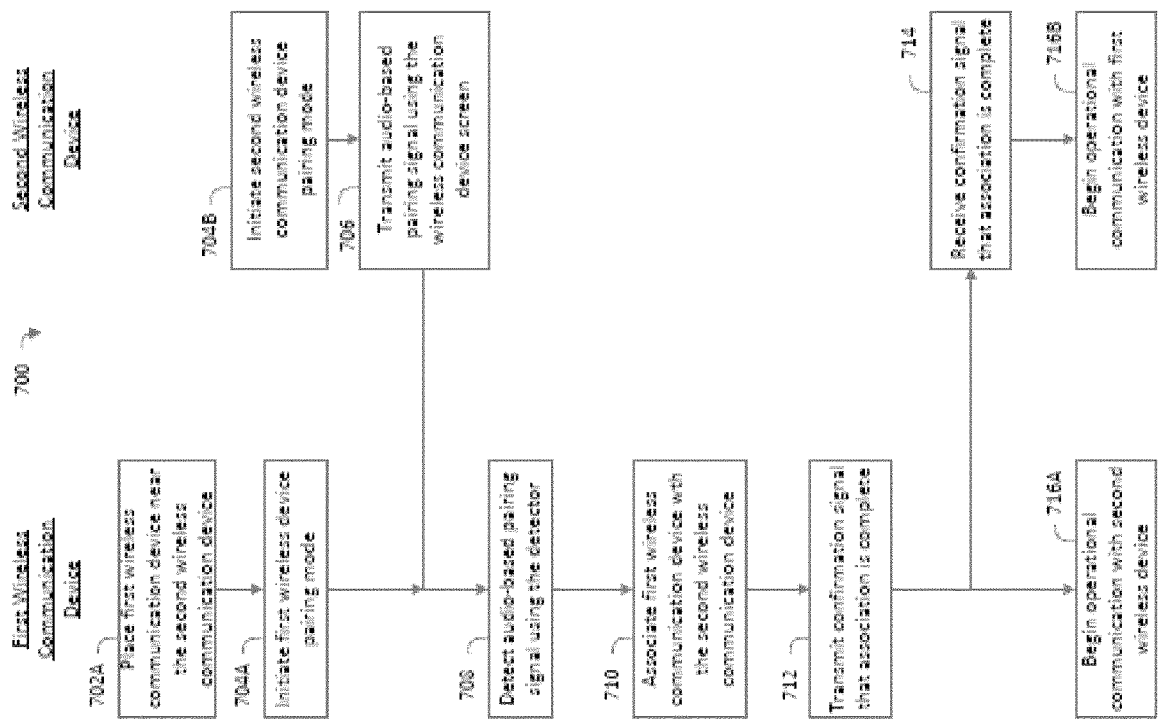
FIG. 7 is a flow diagram describing a process to pair a first wireless device with a second wireless device.

FIG. 7 illustrates another method of associating a first wireless device with a second wireless device, which may be referred to as "pairing." The first wireless device may be a wireless sensor 102 or 202 as described above. The second wireless device may be a mobile device 210 or a beside patient monitor 310 as described above.

At block 702A, the first wireless device may be placed near the second wireless device in preparation for receiving a pairing signal. For sensors that utilize an audio sensor, such as respirator sensor, the pairing signal may be an audio sound or a series of audio sounds. A sound or audio-based detector 147 of the first wireless device may be configured to receive a pairing signal in the form of a sound or audio-based pairing signal. The sounds may be tuned to a frequency within or outside of the range of human hearing and may comprise various rings, chimes, or tones. The series of audio sounds may utilize variations in volume or tone to transmit pairing information. The signal may be unique to the first wireless device and/or the second wireless device. By using a pairing signal that uniquely identifies the first wireless device and/or the second wireless device, a secure connection may be established between the two paired devices.

Various types of sensors can be used with the pairing process of the present disclosure. For example, a pulse oximeter sensor can be paired by facing its light detector toward the display or screen of a second wireless communication device to receive a visual, optical, and/or light based signal. In another example, an ulcer sensor can be paired by receiving a pairing signal in the form of detected motion. Similarly, other types of wireless sensors can be paired using the included detectors. For example, an acoustic sensor can be paired based on audio signals emitted from the second wireless communications device. EEG and ECG wireless sensors can be paired using small electrical impulses from a special conductor included as part of the second wireless communications device. Other sensors can be paired in a similar fashion depending on the specific detectors included on the first wireless communication device.

Returning to block 702A, the first wireless device may be placed in proximity to the second wireless communications device such that the sound or audio detector may receive the sound or audio-based pairing signal. The sound or audio-based pairing signal may have a pairing signal transmission range of up to approximately three inches. The sound or audio-based pairing signal has a pairing signal transmission range of up to approximately six inches. The sound or audio-based pairing signal may have a pairing signal transmission range of up to approximately one foot (i.e., twelve inches) or farther. A skilled artisan will recognize that other ranges can be used for the pairing signal transmission range.

At block 704A the first wireless device is set to operate in a pairing mode. A user may begin by initiating the pairing mode of operation for the first wireless device. This may include powering on the first wireless device, switching the first wireless device to a special pairing state, and/or the like. For example, the first wireless device may include a battery isolator 120 which, when removed, activates the first wireless device. Upon activation, the default mode of operation is the pairing mode. The first wireless device may have a button/switch 124 that can be used to activate the first wireless device and place it in the pairing mode of operation. For example, a depressible button/switch 124 can be located on the top portion of the housing 150. When the button/switch 124 is depressed and continuously held down, the first wireless device enters into the pairing mode of operation and remains in the pairing mode of operation for as long as the button or switch 124 is depressed. The wireless sensor can be placed in pairing mode by being shaken, bounced, or by shining a bright light at the detector. The first wireless device enters into the pairing mode by activating the sound or audio-based sensor 147. Once activated, the sound or audio-based sensor 147 may be configured to receive the audio or sound-based pairing signal.

At block 704B, the second wireless device is set to operate in pairing mode. A user may begin by initiating the pairing mode of operation for the second wireless device. This may include powering on the device, switching the device to a special pairing state, and/or the like. The second wireless device may have a button/switch that can be used to activate the second wireless device and place it in the pairing mode of operation. When the button/switch is depressed and/or continuously held down, the second wireless device enters into the pairing mode of operation.

As reflected at block 706, the second wireless device transmits a pairing signal to pair, or associate, with first wireless device. The second wireless communications device may be configured to emit a pairing signal. The speaker of the second wireless communications device may be configured to emit an audio signal or a series of audio sounds as the pairing signal. The pairing signal transmission is received by orienting the audio or sound-based detector 147 of the first wireless device toward the second wireless communications device. The limited range of the audio or sound-based pairing signal helps to prevent unintended or incidental association of the first wireless device with a second wireless device that might be nearby but which is not intended to be paired with the first wireless device. Such circumstances can occur in residential buildings, office buildings, commercial facilities, airports, public transportation facilities, hospitals, healthcare facilities, nursing homes, and the like where the first wireless communications device and second communications device are located in close physical proximity to one another.

At block 708, the first wireless device detects the pairing signal from second wireless device. Upon detection of the pairing signal, the first wireless device, at block 710, associates with the second wireless device thereby configuring the first wireless device and second wireless device to communicate with each other. Once the pairing is completed, the first wireless device transmits a confirmation signal confirming that the first wireless communication device is associated with the second wireless device, thereby indicating that the pairing process has been successfully completed, as reflected in block 712. At block 714, the second wireless device receives the confirmation signal. And at block 716A, the first wireless device exits the pairing mode of operation and enters into a patient parameter sensing mode of operation. Similarly, at block 716B, the second wireless device enters a patient parameter sensing mode of operation.

Figure 8:
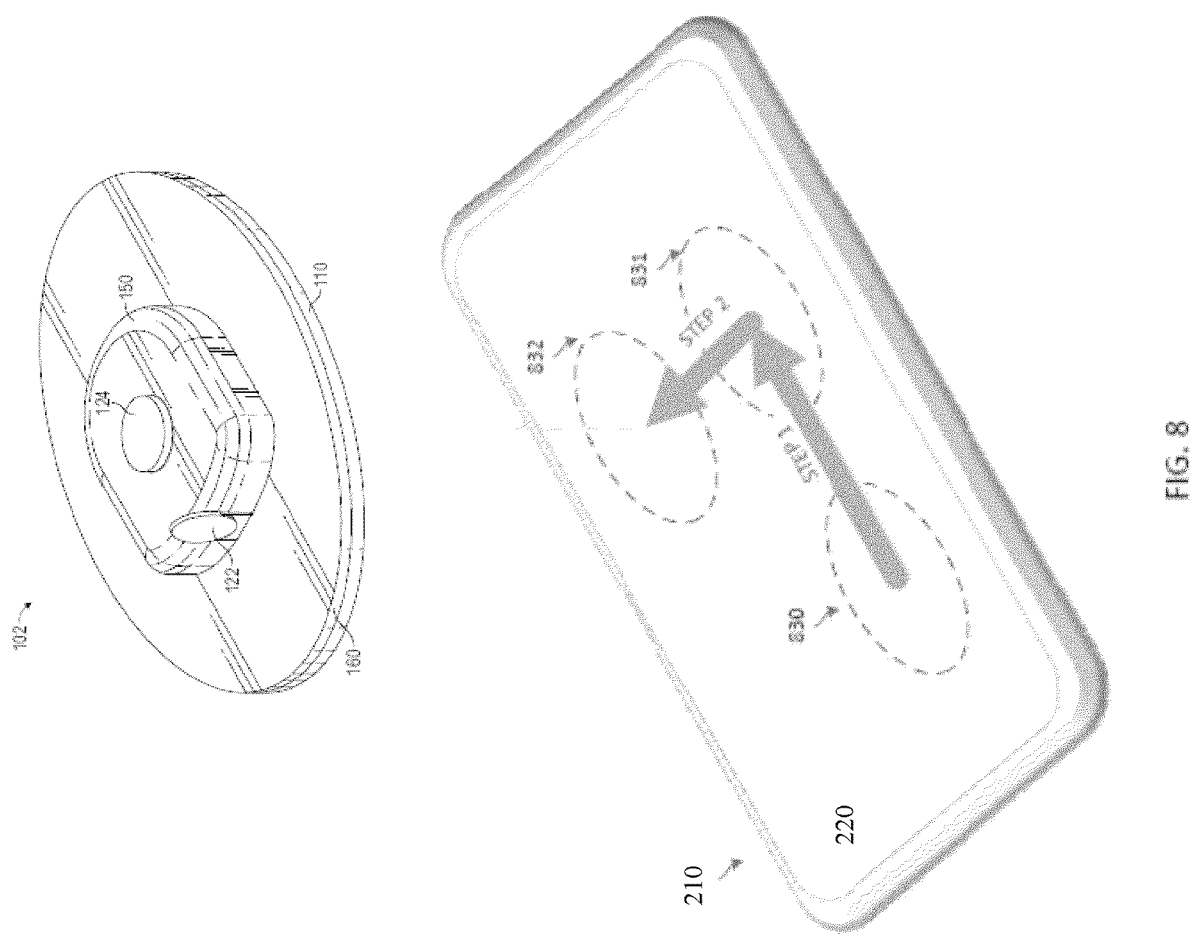
FIG. 8 is a schematic perspective view of the disclosed wireless sensor and a mobile device for pairing.

FIG. 8 illustrates a method of associating a wireless sensor 102 with a wireless communication device 810, which may be referred to as "pairing." A wireless sensor 102 may include a motion sensor. The wireless communication device 810 may include a device screen 820. Here, the pairing signal may involve displaying instructions on device screen 820 for a user to follow. The instructions may indicate steps that a user must follow in order to complete the pairing process. In one example, the instructions may be a sequence of motions that the user must perform on the wireless sensor 802. The instructions may be displayed using objects 830, 831, 832 on device screen 820 representing the silhouette of the wireless sensor 102. The objects 830, 831, 832 are displayed on the device screen 820 in sequence, one at a time, along with an arrow representing the direction the wireless sensor 102 should move. To follow the instructions, the user may hold the wireless sensor 102 and move the position of the wireless sensor 102 according to the instructions. For example, to complete STEP 1 of the pairing instruction, the user will move the wireless sensor 102 in an upward motion relative to the device screen 820. The change in position of first wireless communication device 820 will resemble the relative change in position from object 830 to object 831 on the device screen 820. To complete STEP 2 of the pairing instruction, the user will move the wireless sensor 102 in a leftward motion relative to the device screen 820. The change in position of the wireless communication device 820 will resemble the relative change in position from object 831 to object 832 on the device screen 820. The motion detector of the wireless communication device 810 detects each step of the motion. The detected motion is then used as the pairing signal to associate the wireless sensor 102 with wireless communication device 810. One skilled in the art will appreciate that other types and sequences of motion may be used as the pairing signal.

Figure 9:
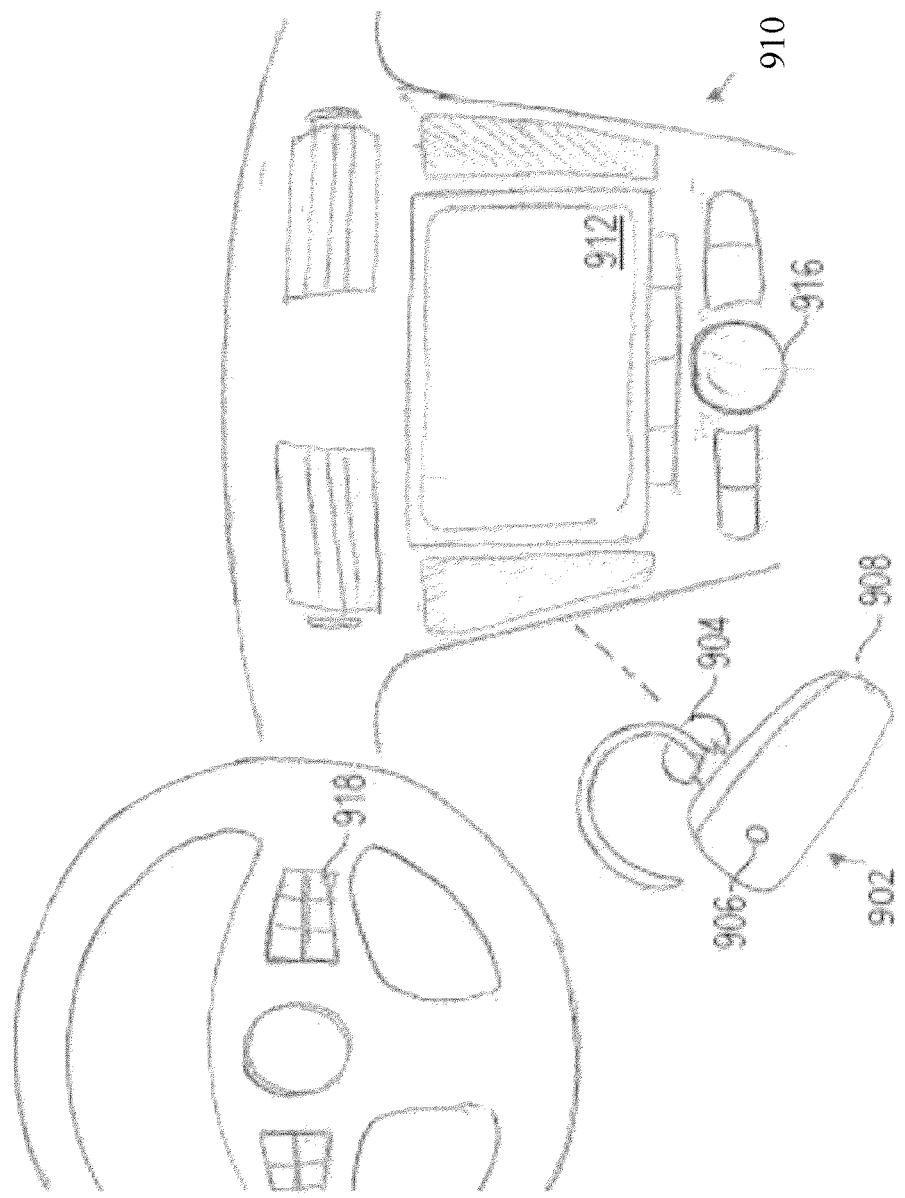
FIG. 9 is a schematic perspective view of the disclosed wireless sensor and a car console for pairing.

FIG. 9 illustrates a method of associating a first wireless communication device with a second wireless communication device. The first wireless communication device may be a bluetooth headset 902. The wireless communication device may be a vehicle console or infotainment system 910. The vehicle console or infotainment system 910 may include a screen 912 for displaying information related to the operation of the vehicle and control interface. The console or infotainment system 910 may receive data such as an audio signal, video signal, GPS location, driving directions, or fare calculations from a paired wireless communication device from a first wireless communication device 902. A skilled artisan would recognize that other data may be exchanged between the vehicle console or infotainment system and a paired wireless communication device.

The transmission of data associated with the functionality of the wireless communication device 902 and vehicle console or infotainment system 910 may be facilitated by a wireless data connection established using a pairing procedure. The pairing procedure may include using a pairing signal to associate the first wireless communication device 902 with vehicle console or infotainment system 910. The pairing signal may contain a pattern containing a shape, color, or a combination of patterns. The pairing signal may contain a series of visual, optical, and/or light based signals. The series of signals may utilize variations in color, shade, shape, or visual patterns. The pairing signal may contain a series of flashes, wherein the flashes may vary in intensity or duration. The wireless communication device 902 may have a light 906 that emits various visual or light based signals. Similarly, the wireless communication device 902 may include a speaker 908 that may generate audio-based pairing signals. The sounds may be tuned to a frequency within or outside of the range of human hearing and may comprise various rings or tones. The pairing signal may comprise a combination of visual signals emitted from wireless communication device light 906 and audio signals emitted from wireless communication device speaker 908. The pairing signal may include a sequence of visual signals emitted from console screen 912 that is synchronized with a sequence of audio signals emitted from console speaker. Additionally, the wireless communication device 902 may have a speaker 904 configured to be placed in the user's ear. The speaker 904 or the speaker 908 may transmit a confirmatory signal that the device has been successfully paired.

The pairing process may be similar to the methods described above. The screen 912 of the vehicle console or infotainment system 910. The pairing signal may involve displaying instructions on the screen 912 for a user to follow. The instructions may include placing a wireless communication device 902 of a particular shape and size in a certain position relative to the screen 912. The user may follow the instructions and hold the wireless communication device 902 in a certain position relative to the screen 912 to pair the wireless communication device 902 to the vehicle console or infotainment system 910.

Additionally, the console screen 912 may be configured to display motion instructions for a user to perform in order to generate motion signals representing a pairing signal. Additionally, the console or infotainment system 910 may have a port for connecting peripheral devices that may generate various signals such as current or voltage based signals. The pair signal may take the form of an electrical signal.

The vehicle console or infotainment system 910 can have a switch or button 916 which, when depressed, places the wireless communication device 902 in a pairing mode of operation, causing the wireless communication device 902 to wait for a pairing signal. Similarly, the vehicle console or infotainment system 910 can have a switch or button 918 on the steering wheel which, when depressed, places the wireless communication device 902 in a pairing mode of operation, causing the wireless communication device 902 to wait for a pairing signal.

Many other variations than those described herein will be apparent from this disclosure. For example, certain acts, events, or functions of any of the algorithms described herein can be performed in a different sequence, can be added, merged, or left out altogether (e.g., not all described acts or events are necessary for the practice of the algorithms). Moreover, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The first wireless communication device and second wireless communication device may be paired without additional components. The first wireless communication may be a wireless sensor. The wireless sensor may be a variety of sensors as described herein, such as a magnetometer which may also be referred to as a compass, a temperature sensor, an acoustic respiration sensor, an electrocardiogram (ECG) sensor, an electroencephalography (EEG) sensor, one or more pulse oximetry sensors, a moisture sensor, a blood pressure sensor, and an impedance sensor. The second wireless communication device may be a mobile device 210 or a bedside patient monitor 310. Similarly, a variety of wireless sensors described herein may be paired to a wireless communication device such as a mobile device or a patient monitoring system. Further, the wireless communication device may also other devices such as phones, tablets, headphones, watches, speakers, computer mice, computer keyboards, wearable devices, audio headsets, virtual reality headsets, augmented reality headsets, vehicle consoles, infotainment systems, and any other wireless communication devices known to those of skill in the art.

The methods and systems described herein can be implemented without any additional hardware components. There is no installation of additional components required. This can provide ease of use and implementation such that users can use devices they are familiar with without additional components. For example, as described above, the shape of the device may be used as a pairing signal. In another example, the vibration of an acoustic sensor may be used as a pairing signal. The properties of the sensors or wireless communication devices can be utilized in the pairing process by the system and methods described herein.

The methods and systems for pairing described herein can also be implemented without the use of wireless communication protocols. For example, the pairing methods and systems can be implemented without the use of protocols such as a Bluetooth protocol, a wifi protocol, or a zigbee protocol.

The various illustrative logical blocks, modules, and algorithm steps described in connection with the disclosure herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the disclosure herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. A processor may include an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the disclosure herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various examples, it will be understood that various omissions, substitutions, and changes in the form and details of the systems, devices or methods illustrated can be made without departing from the spirit of the disclosure. As will be recognized, certain examples described herein can be embodied within a form that does not provide all of the features and benefits set forth herein, as some features can be used or practiced separately from others.

The term "and/or" herein has its broadest, least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Although the foregoing disclosure has been described in terms of certain preferred examples, other examples will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the description of the preferred examples, but is to be defined by reference to claims.

What is claimed is:

1. A system for electronically pairing a wireless physiological sensor with a physiological monitoring device, the system comprising:
   a wireless physiological sensor having a pairing mode and a parameter sensing mode, the wireless physiological sensor comprising a non-invasive detector configured to detect a physiological parameter associated with a patient,
      wherein the pairing mode comprises a mode where the wireless physiological sensor is configured to detect a pairing signal by the same non-invasive detector that is configured to detect the physiological parameter associated with the patient in the parameter sensing mode; and
   one or more hardware processors configured to:
      display a pairing object on a screen of the physiological monitoring device;
      detect a placement of the wireless physiological sensor on the screen in relation to the displayed pairing object;
      associate the wireless physiological sensor with the physiological monitoring device based on the detected placement; and
      configure the wireless physiological sensor to enter into the parameter sensing mode after the wireless physiological sensor is associated with the mobile device.

2. The system of claim 1, wherein the non-invasive detector comprises an optical detector.

3. The system of claim 1, wherein the non-invasive detector comprises an audio detector and wherein the pairing signal further comprises an audio signal.

4. The system of claim 1, wherein the pairing signal is synchronized with a sequence of audio signals.

5. The system of claim 1, wherein the wireless physiological sensor comprises a button or switch configured to activate the pairing mode.

6. The system of claim 1, wherein the pairing object comprises a visual pattern displayed on the screen of the physiological monitoring device, the visual pattern comprising at least one of a shape, shade, pattern, or color associated with the wireless physiological sensor.

7. The system of claim 6, wherein the visual pattern comprises a shape corresponding to a silhouette of the wireless physiological sensor.

8. The system of claim 7, wherein the one or more hardware processors are configured to associate the wireless physiological sensor based on a placement of the wireless physiological sensor at a location on a display of the physiological monitoring device associated with the location of the visual pattern.

9. The system of claim 1, wherein the one or more hardware processors are configured to receive a confirmation signal from the physiological sensor of a successful association.

10. The system of claim 1, wherein the wireless physiological sensor does not require a separate antenna or any additional components for the pairing with the physiological monitoring device.

11. The system of claim 1, wherein the wireless physiological sensor does not use a wireless communication protocol for the pairing with the physiological monitoring device.

12. The system of claim 11, wherein the wireless communication protocol comprises at least one of: a Bluetooth protocol, wifi protocol, or a zigbee protocol.

13. The system of claim 1, wherein the wireless physiological sensor does not require a separate antenna or any additional components for the pairing with the physiological monitoring device.

14. A method for electronically pairing a wireless physiological sensor with a physiological monitoring device, the method comprising:
   receiving an indication for a wireless physiological sensor, having a non-invasive detector configured to detect a physiological parameter associated with a patient to enter a pairing mode, wherein the pairing mode comprises a mode where the wireless physiological sensor is configured to detect a pairing signal by the same non-invasive detector that is configured to detect the physiological parameter associated with the patient while in a parameter sensing mode;
   displaying a pairing object on a screen of a physiological monitoring device;
   detecting a placement of the wireless physiological sensor on the screen in relation to the displayed pairing object;
   associating the wireless physiological sensor with the physiological monitoring device based on the placement; and
   configuring the wireless physiological sensor to enter into the parameter sensing mode after the wireless physiological sensor is associated with the physiological monitoring device.

15. The method of claim 14, wherein the non-invasive detector comprises an optical detector.

16. The method of claim 14, wherein the non-invasive detector comprises an audio detector and wherein the pairing signal further comprises an audio signal.

17. The method of claim 14, wherein the pairing signal is synchronized with a sequence of audio signals.

18. The method of claim 14, wherein the indication comprises a user interaction with a button or switch on the wireless physiological sensor configured to activate the pairing mode.

19. The method of claim 14, wherein the pairing object comprises a visual pattern displayed on the screen of the physiological monitoring device, the visual pattern comprising at least one of a shape, shade, pattern, or color associated with the wireless physiological sensor.

20. The method of claim 19, wherein the visual pattern comprises a shape corresponding to a silhouette of the wireless physiological sensor.

21. The method of claim 14, wherein associating the wireless physiological sensor is based on a placement of the wireless physiological sensor at a location on a display of the physiological monitoring device associated with the location of the visual pattern.

\* \* \* \* \*